United States Patent
Yuds et al.

(10) Patent No.: US 11,710,555 B2
(45) Date of Patent: Jul. 25, 2023

(54) MEDICAL SYSTEM WITH DOCKING STATION AND MOBILE MACHINE

(71) Applicant: Fresenius Medical Care Holdings, Inc., Waltham, MA (US)

(72) Inventors: David Yuds, Hudson, NH (US); Samiullah K. Durrani, Harvard, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 404 days.

(21) Appl. No.: 16/726,391

(22) Filed: Dec. 24, 2019

(65) Prior Publication Data
US 2021/0193303 A1    Jun. 24, 2021

(51) Int. Cl.
*G16H 40/20* (2018.01)
*G16H 40/67* (2018.01)
(Continued)

(52) U.S. Cl.
CPC .............. *G16H 40/20* (2018.01); *A61M 1/14* (2013.01); *G16H 40/63* (2018.01); *G16H 40/67* (2018.01);
(Continued)

(58) Field of Classification Search
CPC ........ G16H 40/20; G16H 40/63; G16H 40/67; A61M 1/14; A61M 2205/33;
(Continued)

(56) References Cited

U.S. PATENT DOCUMENTS 7,283,810 B1 * 10/2007 Arakawa .................. G08G 1/20
340/459
2001/0037163 A1    11/2001 Allard
(Continued)

FOREIGN PATENT DOCUMENTS

AU          736366       6/2000
AU       1999047353      6/2000
(Continued)

OTHER PUBLICATIONS

Prescott et al., "IntelliTable: Inclusively-designed furniture with robotic capabilities," Studies in health technology and informatics, 2017, 242:565-572.
(Continued)

*Primary Examiner* — Jason S Tiedeman
*Assistant Examiner* — Liza Tony Kanaan
(74) *Attorney, Agent, or Firm* — Fish & Richardson P.C.

(57) ABSTRACT

A computer-implemented medical system is provided. The system includes a docking station and a mobile machine. The system is configured to perform operations comprising: receiving, by the mobile machine and from a user, a request to transport the mobile machine to a target location to perform a medical treatment; automatically navigating the mobile machine to the target location; performing, by the mobile machine, the medical treatment on a patient; determining, by the mobile machine, that the medical treatment is completed and the mobile machine is disconnected from the patient; automatically navigating the mobile machine to a stationary docking station of the medical system; and determining that the mobile machine is connected to the docking station through one or more connectors, and in response, receiving, by the mobile machine, at least one of an electrical charge, a refill of one or more supplies, a cleaning, or a drain of waste.

24 Claims, 6 Drawing Sheets

(51) Int. Cl.
*G16H 40/63* (2018.01)
*A61M 1/14* (2006.01)
*H04W 4/02* (2018.01)

(52) U.S. Cl.
CPC ........ *H04W 4/025* (2013.01); *A61M 2205/33* (2013.01); *A61M 2205/35* (2013.01); *A61M 2205/58* (2013.01)

(58) Field of Classification Search
CPC .......... A61M 2205/35; A61M 2205/58; A61M 1/168; A61M 2205/3584; A61M 2205/6018; A61M 2205/70; A61M 2205/8237; A61M 2209/01; A61M 2209/045; A61M 2209/10; H04W 4/025; A61B 50/13
See application file for complete search history.

(56) References Cited

U.S. PATENT DOCUMENTS

| | | | |
|---|---|---|---|
| 2003/0030398 A1 | 2/2003 | Jacobs et al. | |
| 2005/0156562 A1 | 7/2005 | Cohen et al. | |
| 2007/0156286 A1 | 7/2007 | Yamauchi | |
| 2012/0286730 A1* | 11/2012 | Bonny | B60L 53/14 320/109 |
| 2013/0117959 A1 | 5/2013 | Stryker et al. | |
| 2013/0133036 A1 | 5/2013 | Wang et al. | |
| 2013/0310726 A1 | 11/2013 | Miller et al. | |
| 2014/0081656 A1* | 3/2014 | Alamri | G16H 40/20 705/3 |
| 2014/0100693 A1 | 4/2014 | Fong et al. | |
| 2014/0213962 A1 | 7/2014 | Marterstock | |
| 2014/0263087 A1 | 9/2014 | Renaud et al. | |
| 2014/0277894 A1* | 9/2014 | Doyle | B60W 10/26 701/23 |
| 2014/0330452 A1 | 11/2014 | Stewart | |
| 2015/0095041 A1 | 4/2015 | Kim | |
| 2015/0119638 A1* | 4/2015 | Yu | A61B 1/018 600/102 |
| 2015/0216746 A1* | 8/2015 | Dirauf | A61G 7/012 701/25 |
| 2016/0100521 A1 | 4/2016 | Holloran et al. | |
| 2016/0184032 A1* | 6/2016 | Romo | B25J 9/1682 606/130 |
| 2017/0049288 A1* | 2/2017 | Knutson | A47L 11/4083 |
| 2017/0340792 A1* | 11/2017 | Shyam | H01M 16/006 |
| 2018/0361045 A1 | 12/2018 | Griessmann | |

FOREIGN PATENT DOCUMENTS

| | | |
|---|---|---|
| CN | 109240103 | 1/2019 |
| DE | 102018114476 | 8/2019 |
| EP | 3416073 | 12/2018 |
| KR | 10-2033325 B1 | 10/2019 |
| WO | WO 2013/074635 | 5/2013 |
| WO | WO 2013/173349 | 11/2013 |
| WO | WO 2014/055966 | 4/2014 |

OTHER PUBLICATIONS

PCT International Search Report and Written Opinion in International Appln. No. PCT/US2020/064818, dated Mar. 30, 2021, 15 pages.

* cited by examiner

MEDICAL SYSTEM WITH DOCKING STATION AND MOBILE MACHINE

TECHNICAL FIELD

This disclosure relates to methods and medical systems that can be used for medical treatments, for example, personal medial systems such as hemodialysis and peritoneal dialysis machines.

BACKGROUND

Personal health care systems, such as home dialysis machines, have provided patients the convenience of monitoring and controlling their chronic diseases at home and have eliminated a need for frequent visits to medical clinics for such purposes. Such systems are usually bulky and require particular facilities, such as proper plumbing and electrical connections, in order to be stored and operable. Usually, users dedicate a particular part of their homes or other place of residence for storing and operating such systems.

SUMMARY

Implementations of the present disclosure include computer-implemented methods and systems that improve efficiency in storing and using medical devices, such as bulky personal medical dialysis systems. Each of the medical systems disclosed herein can include a mobile machine and a docking station. The mobile machine can navigate itself from a source location (e.g., from the docking station) to a destination location (e.g., a location where a user can use the machine for a medical treatment). The docking station can recharge, refill, clean, and/or drain waste from the mobile machine.

Users of medical devices usually store such devices at particular locations (e.g., closets) and retrieve those devices to use them for medical treatments. One problem with this procedure is that small medical devices can easily be lost. As the size of a medical device gets bigger, the chance of losing it reduces. However, as the size of a medical device gets larger, the locations where the device can be stored gets more limited. This problem gets worse when such medical devices require particular facilities such as particular electrical connections or plumbing. For example, dialysis machines such as hemodialysis (HD) and peritoneal dialysis (PD) machines usually require to be set up in locations where plumbing is available to drain effluents or other liquid wastes. Because of these requirements, some users set up those machines in the kitchen, bathroom, or a dedicated closet where the required plumbing or electrical facilities are available for those machines. However, users of such bulky devices may need to use them frequently (e.g., on a daily or weekly basis) and storing such devices in isolated locations such as closets may not be convenient. Storing medical devices in common areas (e.g., living room or bedroom of a place of residence) may also not be convenient or desirable because the user would lose a sense of home or may not be able to hide those devices or the user's chronic disease from visitors or guests.

Implementations of the present disclosure provide solutions to these problems. The implementations disclose a two-part medical system including a stationary docking station and a dynamic mobile machine. The mobile machine can be summoned by a user to perform medical treatments on the user. Thus, the chance of losing the medical device carried by the mobile machine is reduced. The docking station can be stored in a closet or other isolated locations of a building (e.g., the user's house) and can recharge, refill, clean, or drain waste from the mobile machine. Accordingly, the user can store the medical system in isolated or hidden parts (e.g., closet, laundry, etc.) of the user's place of residence, and can call the mobile machine to any location of the residence when the user wants to perform a medical treatment by the mobile machine.

In an aspect, an example medical system presented herein performs operations including: receiving, by a mobile machine of the medical system and from a user, a request to transport the mobile machine to a target location to perform a medical treatment; automatically navigating the mobile machine to the target location; performing, by the mobile machine, the medical treatment on a patient; determining, by the mobile machine, that the medical treatment is completed and the mobile machine is disconnected from the patient; automatically navigating the mobile machine to a stationary docking station of the medical system; and determining that the mobile machine is connected to the docking station through one or more connectors, and in response, receiving, by the mobile machine, at least one of an electrical charge, a refill of one or more supplies, a cleaning, or a drain of waste.

In some implementations, the mobile machine includes a base machine and a medical treatment device, wherein the base machine transports the medical treatment device from the target location to the docking station. In some implementations, the mobile machine includes at least one of a hemodialysis machine or a peritoneal dialysis machine.

The operations can further include automatically transporting the mobile machine to a storage area designated for storing the mobile machine, the storage area being different from the target location.

The operations can further include: determining that the liquid waste does not have any hazardous material, and in response, causing the liquid waste to be drained from the mobile machine into a primary reservoir; and determining that the liquid waste includes hazardous material, and in response, causing the liquid waste to be drained to a secondary reservoir designated for hazardous material and different from the primary reservoir.

In some implementations, the operations further include determining that a supply of medical material in a supply container is below a threshold amount, and in response, providing an alert.

In some implementations, the mobile machine automatically connects to the docking station through one or more electrical connectors and tubes. In some implementations, the mobile machine receives the request from an electronic device though a wireless network.

Systems and computer-readable medium storing one or more instructions executable by a computer system to perform the above-identified actions and other actions described below are presented herein.

In an aspect, an example medical system includes a stationary docking station and a mobile machine. The mobile machine is connectable to the docking station through one or more electrical connectors and tubes, the mobile machine comprising a medical treatment device operable to perform a medical treatment on a patient. The mobile machine is configured to perform operations including: receiving, from a user, a request to transport the mobile machine to a target location to perform a medical treatment, automatically navigating to the target location, performing the medical treatment on the patient, determining that the medical treatment is completed and the mobile machine is disconnected from the patient, and automatically navigating to the docking station. The docking station is configured to perform operations including determining that the mobile machine is connected to the docking station through one or more connectors, and in response, causing the mobile machine to be charged, refilled, or cleaned.

In some implementations, the mobile machine further includes a base machine. The operations can cause the base machine to transport the medical treatment device. In some implementations, the mobile machine includes at least one of a hemodialysis machine or a peritoneal dialysis machine.

The mobile machine can be configured to automatically transfer the mobile machine to a storage area designated for storing the mobile machine, the storage area being different from the target location.

The docking station can be configured to perform operations including: determining that the liquid waste does not have any hazardous material, and in response, causing the liquid waste to be drained from the mobile machine into a primary reservoir; and determining that liquid drained from the mobile machine includes hazardous material, and in response, causing the liquid waste to be drained to a secondary reservoir designated for hazardous material and different from the primary reservoir.

In some implementations, at least one of the mobile machine or the docking station is to detect that a supply in a supply container is lower than a threshold volume or amount, and in response, providing an alert.

The mobile machine can automatically connects to the docking station through one or more electrical connectors and tubes.

Methods to execute above-identified actions and computer-readable medium storing one or more instructions executable by a computer system to perform the above-identified actions and other actions described below are presented herein.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Figure 1A:
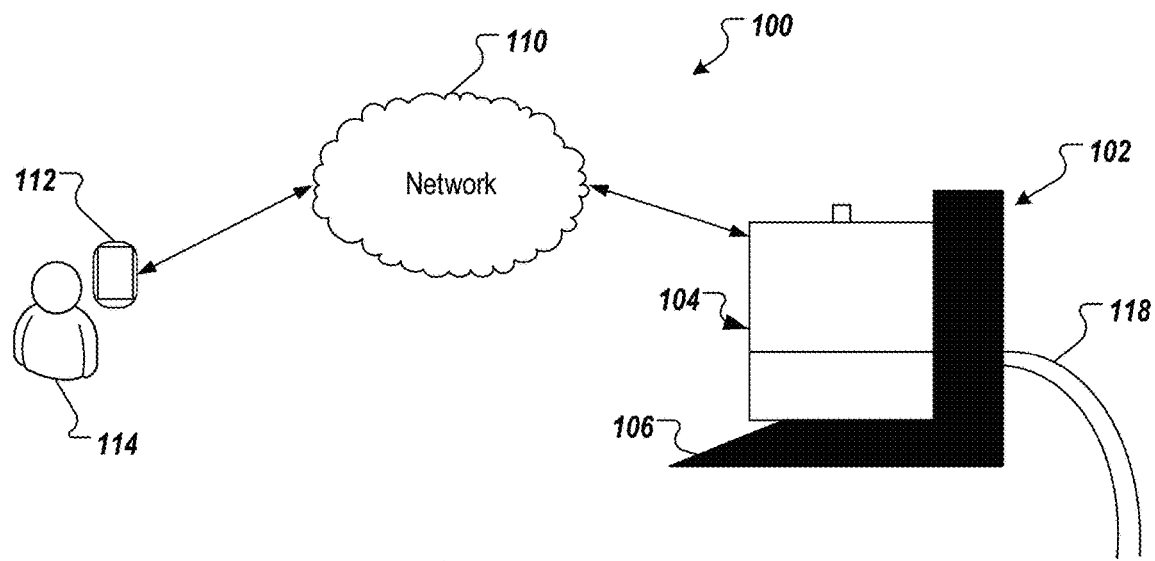
FIGS. 1A and 1B depict example applications of medical systems according to the present disclosure.

FIG. 1A depicts an example communication 100 between a user 114 and a computer-implemented medical system 102 according to the present disclosure. The medical system 102 includes two main parts: a docking station 106, and a mobile machine 104. The docking station 106 is stationary and is configured to drain waste, clean containers, recharge batteries, refill supplies, etc. of the mobile machine 104. The docking station can be connected to utility supplies and reservoirs such as plumbing reservoirs, water and/or other liquid sources, electrical sources, etc. As is described in further details with respect to FIG. 3 below, the mobile machine 104 pulls, pushes, or carries a medical device that the user 114 can use to perform one or more medical treatments.

Figure 1B:
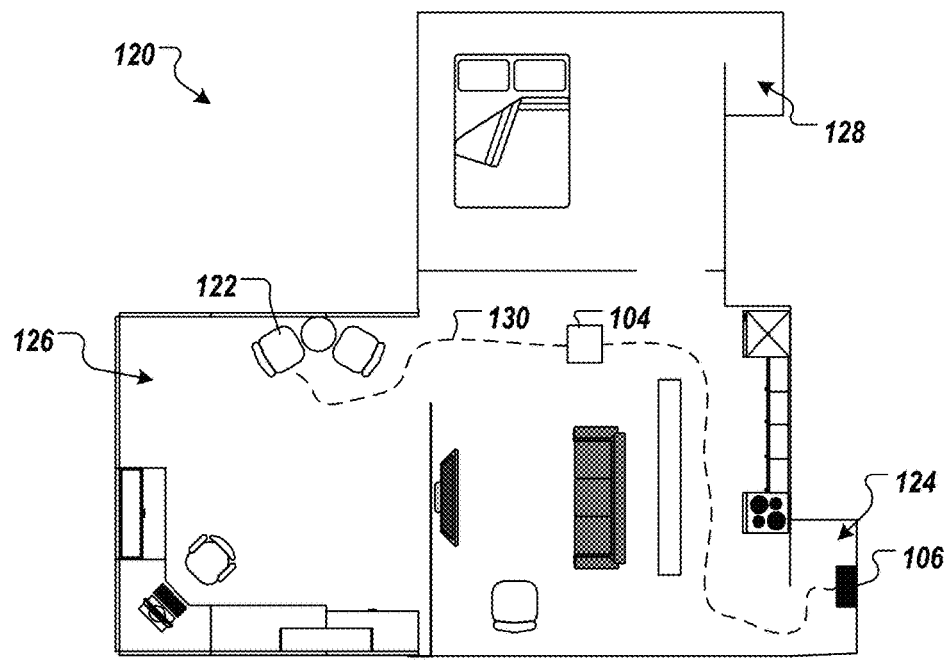

The user 114 can summon the mobile machine 104 to navigate to a target (e.g., treatment) location so that the user can perform the medical treatment at that target location. FIG. 1B illustrates a house 120 as an example environment where the medical system 102 can be used. The user can summon the mobile machine 104 to move to any target location of the house. In the depicted example, the user 114 has selected a chair 122 in a study room 126 as the target location and has summoned the mobile machine 104 to move close to the chair 122. In other cases, the user 114 may select any location in the house 120 as the target location, for example, a location in the bedroom, bathroom, living room, etc.

At the target location, the user can use the mobile machine 104 to perform a medical treatment. The treatment can be performed on the user 114 and or another user (e.g., a patient). Upon completing the medical treatment, the mobile machine 104 automatically determines whether the mobile machine 104 is safely disconnected from the user (e.g., the user 114 or another user receiving the treatment). Once the mobile machine 104 determines that it is safely disconnected from the user, the mobile machine 104 automatically navigates itself to the docking station 106.

The docking station 106 can be stationary and can be set up at any desired part of the house 120. For example, the user can hide the docking station 106 at an isolated part of the house such as a closet 124 or a bathroom. Thus, the user does not have to set up the docking station where the user performs the medical treatments; rather the user can store the docking station 106 and the mobile machine 104 at one or more locations different from the treatment location (e.g., the target treatment location). In this way, the user does not have to move to where the medical system 102 is located for each treatment session, and can rather call the medical system 102 to move to e.g., anywhere in the bedroom, study room 126, living room, etc. for the treatment.

Another benefit is that such configuration improves safety. The medical systems presented herein provide the capability of setting up the system where proper plumbing, electrical connections, source liquids, etc. are provided within the building (e.g., the user's house) rather than where the user wants to perform the medical treatment. For example, if the user usually performs a treatment in bed, the docking station can be stored at a bathroom where proper plumbing is provided, while the mobile machine 104 can be summoned to the user's bedside when needed. Such feature improves user and building safety because it eliminates a need to transport the waste or supplies between different rooms of a building (e.g., through additional pipes or electrical connectors) and reduces potential leakage of the supply and/or waste within the building. In addition, the medical system improves patient's safety by eliminating a need for the patient to carry or dispose medical supplies or waste fluids, such as a need for heavy and/or cumbersome transport of fluids. Rather, the present systems automatically transport medical supplies and/or waste fluids to and from the patient, as well as separate the supplies and/or wastes based on what the material they contain (e.g., hazardous versus medically safe materials).

When the mobile machine 104 reaches to the docking station 106, the mobile machine 104 gets connected to the docking station 106 through one or more connections. The connections can include particular tube connectors such as through tapered tubing, particular electrical connectors such as through magnetic connections, etc. In some implementations, the mobile machine 104 is capable of automatically connecting itself to the docking station 106. In some implementations, the mobile machine 104 may need an operator's assistance for proper connection and/or to check that the connectors are safely connected. For example, the mobile machine 104 may alert the user by generating particular sounds or sending notifications on the user's electronic device 112, informing the user that the machine needs to be connected to the docking station 106.

Once the medical system 102 detects that the mobile machine 104 is safely and properly connected to the docking station 106, the docking station 106 starts performing one or more operations on the mobile machine 104. For example, the docking station 106 can clean, recharge, refill, and/or drain waste (e.g., liquid waste) from the mobile machine 104. The docking station 106 can be connected to utility sources such as electrical, water, gas, etc. to recharge, refill, and/or clean the mobile machine 104. The docking station 106 can be connected to sewage or other waste reservoirs, e.g., through the pipe 108, to drain wastes from the mobile machine 104.

In some implementations, the docking station 106 is connected to multiple waste reservoirs (e.g., two waste reservoirs). The docking station 106 may drain the waste into either of the two waste reservoirs based on one or more health-related concerns. For example, the docking station 106 can drain into a primary reservoir non-hazardous liquid wastes such as usual effluents, water from washing a container of the mobile machine 104, etc. If the docking station 106 and/or the mobile machine 104 detects one or more health hazards in the liquid waste, the docking station 106 may drain the liquid waste into a secondary reservoir designated for such purposes. For example, the primary reservoir may be a city sewage system, a house's septic system, etc. The secondary reservoir may be a particular tank stored inside or outside the house for keeping hazardous waste.

The medical system 102 can be set up to detect one or more hazardous materials such as blood, infections, particular bacteria, particular minerals, etc. in liquid waste at any point before draining the liquid waste. For example, a hazardous material such as blood may be set up to be detected during performing the medical treatment, while another hazardous material such as particular bacteria may be set up to be detected when the mobile machine is connected to the docking station 106.

For example, upon detecting blood or an infection in a dialysis effluent, the docking station 106 and/or the mobile machine 104 of the medical system 102 can determine that it is not safe to drain the liquid into the city sewage, and rather drain it into a tank located outside the house for this purpose. The tank may be emptied on a regular basis, or upon determining that it has been filled up to a particular level. A designated health-related company may empty the tank when needed.

When the docking station's 106 operations on the mobile machine 104 is completed, the mobile machine 104 may stay connected to the docking station 106 until it receives the next user request, or may move to another location that the user may have allocated for storing the mobile machine 104. For example, while the user has set up the docking station 106 in closet 124, the user may decide to keep the mobile machine 104 in the closet 128, for example, to be reminded of the medical treatments that the user needs to perform routinely. Unless the mobile machine 104 is summoned, it can stay in the closet 128 until it needs to be recharged, refilled, and/or cleaned.

The mobile machine 104 can automatically navigate its way through the house 120 to get to the user's target treatment location, to the docking station 106, and/or to the storage location (or area) designated for the mobile machine 104. In some implementations, a map of the house 120 is input (e.g., downloaded) into a storage memory (e.g., storage device 530 of FIG. 5) of the medical system 102, for example, on the mobile machine 104. For example, the map can be input to the storage memory when the medical system 102 is set up (e.g., initially set up) for operation in the house 120, or the map can be built and improved as the mobile machine 104 runs through the house 120 and finds its way through different walls and barriers.

The mobile machine 104 is capable of detecting barriers in order to find its way to its destination location (e.g., the target location 122). For example, the mobile machine 104 in FIG. 1B uses a map of the house to detect the target location 122, and uses its capabilities to detect barriers (e.g., sofa, stove, walls, etc.) to find its path 130 to the target location 122. The mobile machine 104 includes one or more sensors (not shown) such as cameras, light detector sensors, etc. to detect barriers and/or electronically "painted" targets.

The user can select the target treatment location and/or the storage location by selecting such locations on the map, for example, on user electronic device 112. The user electronic device 112 can communicate such selections to the medical system 102 through the network 110. Alternatively, or in addition, the user can paint a particular location of the house 120 for the mobile machine 104 to recognize. For example, when the chair 122 is within an angle of view of one or more sensors of the mobile machine 104 (e.g., when the mobile machine is in room 126), the user may apply a visual laser target to the chair 122, and the mobile machine 104 may detect the laser target and move to the chair 122.

The user 114 can communicate with a receiving component of the medical system 102 by sending and/or receiving messages to the receiving component through the user's electronic device 112 and over a network 110. For example, the electronic device 112 can send information of the target location to the medical system 102 and request the mobile machine 104 to move to that target location. Examples of the electronic device 112 can include a personal computer, laptop, smartphone, electronic dispatcher, etc. The network 110 can be wireless network or a wired network. The network 110 can be a local network such as WiFi, Bluetooth, etc., or a non-local network such as a cellular network.

Alternatively, or in addition, the user may summon the mobile machine 104 by calling a particular name or phrase recognizable by the mobile machine 104. The particular name or phrase can be programed on a processor of the medical system 102 to activate a voice recognition module on the system. The voice recognition module receives the spoken name or phrase to determine whether the spoken name or phrase matches a code word associated with a respective action stored on a memory of the medical system 102, such as a transportation of the mobile machine 104 to a particular location. In response to finding a match, the medical system 102 performs the respective action.

Upon receiving the user's request (or summon), the mobile machine 104 moves from a source location to the location that the user has requested. The source location can be the location where the user typically stores the mobile machine 104, a location where the user had used the mobile machine 104 for a prior medical treatment, or anywhere else the mobile machine 104 was located when it received the user's request.

The medical system 102 can communicate with a health care provider of the user to report information such as medical treatments performed on the user, any concerns on the medical treatment, any health issues with the user, a history of the mobile machine 104's usage, etc. For example, if the medical system 102 determines that the user has not used the medical system 102 for longer than a specified period of time (e.g., over two weeks for a medical treatment that needs to be done weekly), the system may notify the user's health care provider about this issue. As another example, if the system determines abnormalities in the user's health such as high blood pressure, blood in user's effluent, etc., the system can alert the user's health care provider about this issue. The medical system 102 can communicate to the health care provider through a wireless and/or wired network.

Figure 3:
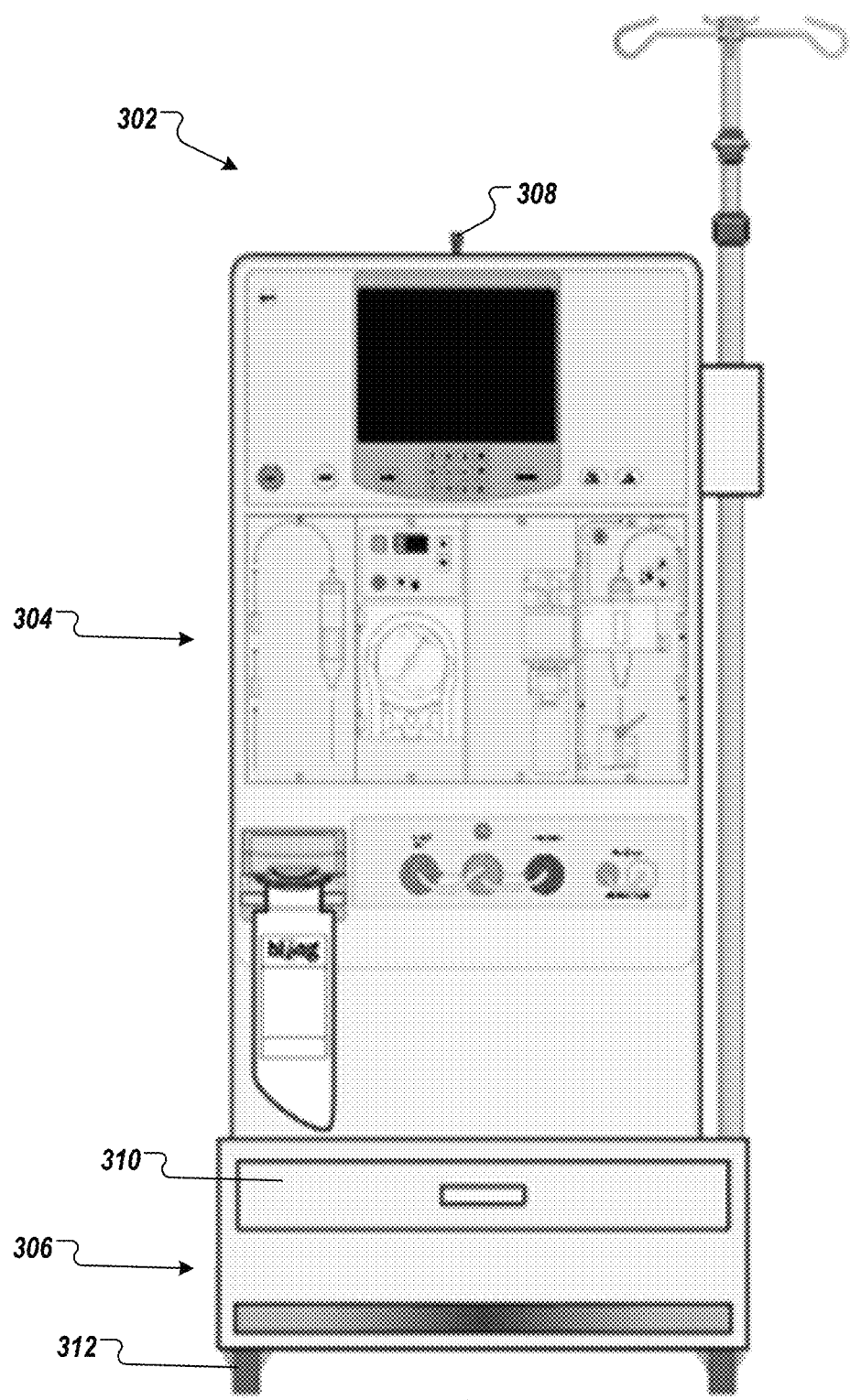
FIG. 3 depicts an example mobile machine according to implementations of the present disclosure.

FIG. 3 provides an example mobile machine 302, according to embodiments of the present disclosure. The mobile machine 302 can be an example of the mobile machine 104 in FIG. 1A. The mobile machine 302 includes two main parts: a medical device 304, and a base machine 306. In this particular example, the base machine 306 carries the medical device 304 to move the medical device 304 from a source location to a destination location. In other examples, the base machine 306 may push or pull the medical device 304. The base machine 306 moves the medical device 304 to the desired locations such as the target treatment location 122.

The base machine 306 can be manufactured with a particular setup designed for connection with a particular medical device, or can be manufactured with a default setup configured to allow the base machine 306 be connected to a variety of the medical devices. For example, the base machine 306 may be manufactured and/or sold separately from the medical device 304, and may be configured to be connected, for example, to any type of dialysis machine, blood pressure measurement device, etc.

The base machine 306 includes one or more transportation wheels (e.g., wheel 312). At least one wheel of the one or more transportations wheels may automatically get locked when the mobile machine 302 detects that a user is using the medical device 304 for a medical treatment. The wheel 312 can also be locked when the docking station is performing an operation on the mobile machine 302. The mobile machine 302 includes a receiver component 308 (e.g., an antenna) configured to communicate with a docking station (e.g., the docking station 106 of FIG. 1A), with a user electronic device (e.g., the electronic device 114 of FIG. 1A), or with other computing systems through a network (e.g., the network 110 of FIG. 1A).

Each of the base machine 306 and the medical device 304 can include one or more respective containers (e.g., the container 310 of FIG. 1A) to store medical supplies such as gauze, tape, syringe, medicine, etc. In some implementations, upon detecting that one or more medical supplies of the base machine 306 and/or the medical device 304 is running low, the docking station automatically refills such supplies. In some implementations, the mobile machine 302 or the docking station sends a notification to the user's electronic device (e.g., 112), notifying the user about the need to refill the respective supply.

Any of the docking station (e.g., the docking station 106 of FIG. 1A) and the mobile machine 302 can detect that a medical supply is running low by measuring a weight of a container that stores the medical supply, and/or by reading smart-tags on the remaining supplies stored in the container and counting the number of tags associated with the respective supplies. For example, each supply container in the mobile machine 302 may be equipped with a respective weight and/or volume sensor that measures the weight and/or the volume of the supply stored in the container. Upon detecting that the weight and/or volume of the supply is below a respective predetermined threshold, the docking station or the mobile machine 302 may detect that the supply is running low.

Figure 2A:
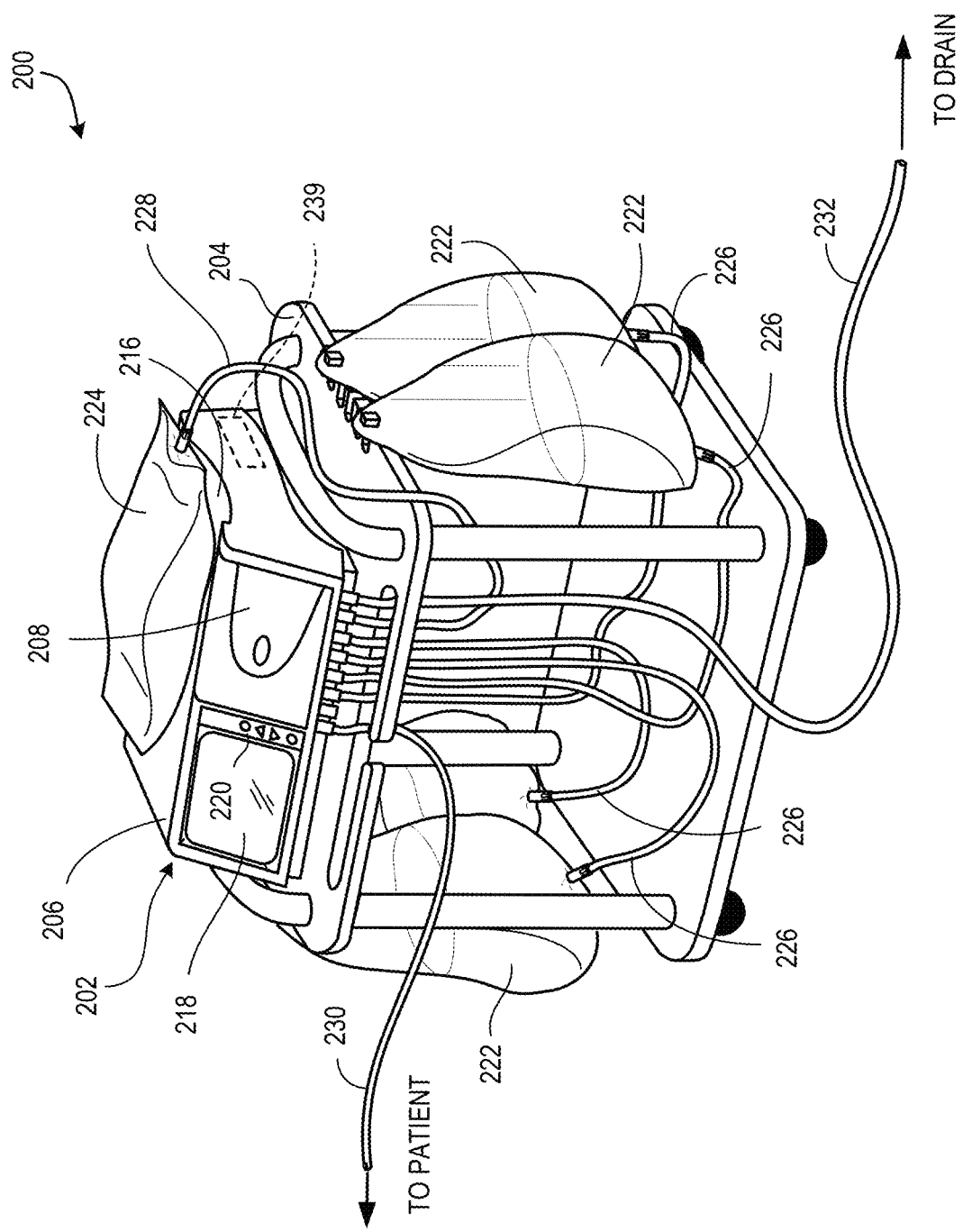
FIG. 2A depicts an example peritoneal dialysis (PD) system as part of an example mobile machine according to the present disclosure.
Figure 2B:
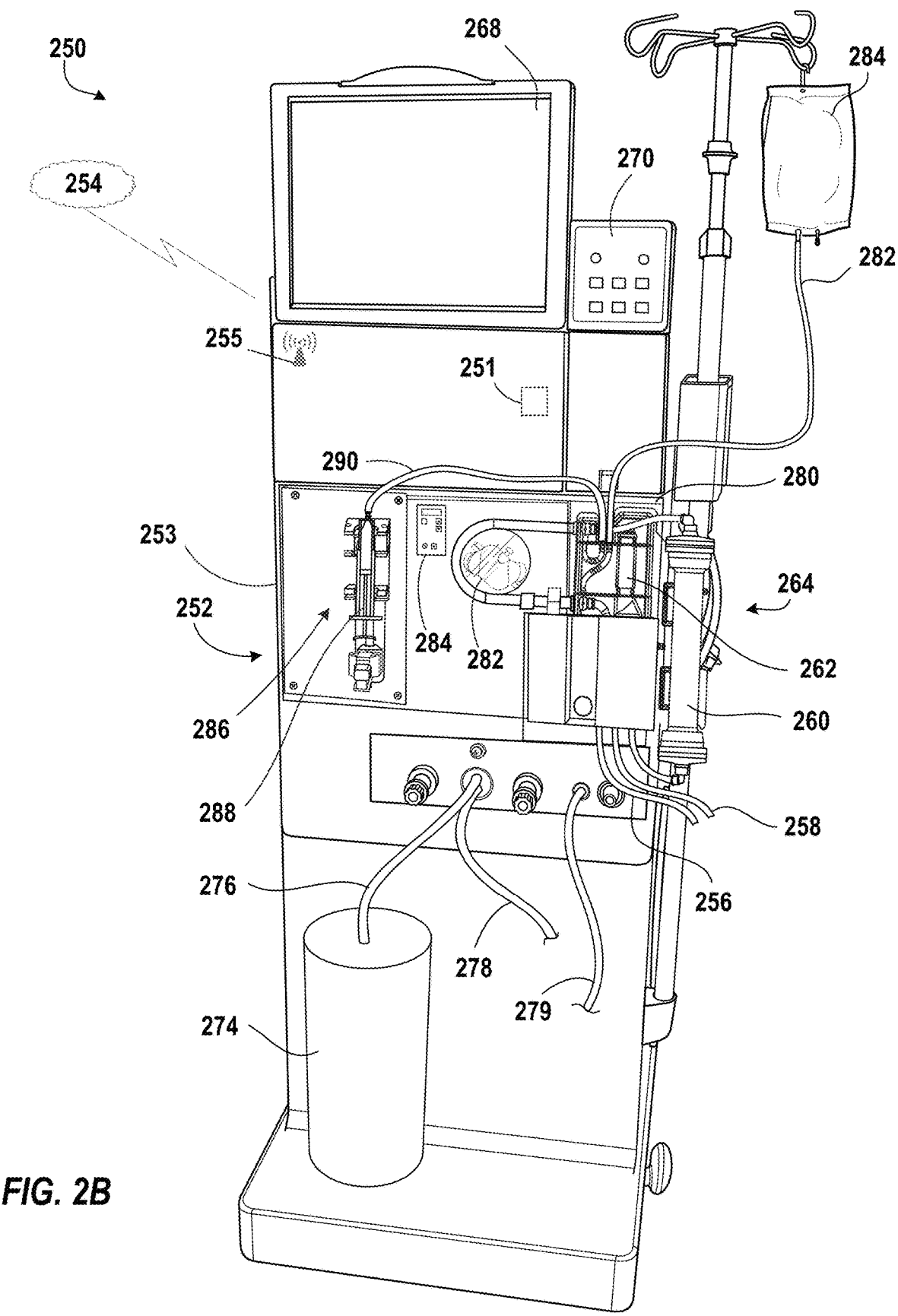
FIG. 2B depicts an example hemodialysis (HD) system as part of an example mobile machine according to the present disclosure.

The medical device 304 is configured to perform one or more medical treatments on the user. Some example medical devices are depicted in FIGS. 2A and 2B. FIG. 2A depicts an example peritoneal dialysis (PD) system 200, and FIG. 2B depicts an example hemodialysis (HD) system 250. Although the present medical device examples are described with reference to dialysis machines including PD machines and HD machines, the disclosed medical system can be implemented for use on any other healthcare devices used for treatment, monitoring, or assisting a user with one or more medical issues.

The PD system 200 in FIG. 2A and the HD system 250 in FIG. 2B show example medical devices that can be implemented as the mobile machine 104 of FIG. 1A and/or the mobile machine 302 of FIG. 3. For example, the PD machine 202 in the PD system 200, or the HD machine 252 of the HD system 250, can be a medical device carried, held, pushed, and/or pulled by a base machine, such as the base machine 306 shown in FIG. 3.

In some implementations, the PD system 200 is configured for use at a patient's home (e.g., a home PD system). In some implementations, the HD system 250 is configured for use at a patient's home (e.g., a home HD system).

The PD system 200 includes a PD machine (also generally referred to as a PD cycler) 202 seated on a cart 204. The PD machine 202 includes a housing 206, a door 208, and a cassette interface 210 that contacts a disposable PD cassette 212 when the cassette 212 is disposed within a cassette compartment 214 formed between the cassette interface 210 and the closed door 208. A heater tray 216 is positioned on top of the housing 206. The heater tray 216 is sized and shaped to accommodate a bag of PD solution such as dialysate (e.g., a 5 liter bag of dialysate). The PD machine 202 also includes a user interface such as a touch screen display 218 and additional control buttons 220 that can be operated by a user (e.g., a caregiver or a patient) to allow, for example, set up, initiation, and/or termination of a PD treatment.

Dialysate bags 222 are suspended from fingers on the sides of the cart 204, and a heater bag 224 is positioned in the heater tray 216. The dialysate bags 222 and the heater bag 224 are connected to the cassette 212 via dialysate bag lines 226 and a heater bag line 228, respectively. The dialysate bag lines 226 can be used to pass dialysate from dialysate bags 222 to the cassette 212 during use, and the heater bag line 228 can be used to pass dialysate back and forth between the cassette 212 and the heater bag 224 during use. In addition, a patient line 230 and a drain line 232 are connected to the cassette 212. The patient line 230 can be connected to a patient's abdomen via a catheter and can be used to pass dialysate back and forth between the cassette 212 and the patient's peritoneal cavity during use. The catheter may be connected to the patient line 230 via a port such as a fitting. The drain line 232 can be connected to a drain or drain receptacle and can be used to pass dialysate from the cassette 212 to the drain or drain receptacle during use.

The PD machine 202 also includes a control unit 239 (e.g., a processor). The control unit 239 can receive signals from and transmit signals to the touch screen display 218, the control panel 220, and the various other components of the PD system 200. The control unit 239 can control the operating parameters of the PD machine 202. In some implementations, the control unit 239 is an MPC823 PowerPC device manufactured by Motorola, Inc.

The HD system 250 illustrated in FIG. 2B includes an HD machine 252 to which a disposable blood component set 264 that forms a blood circuit is connected. During hemodialysis, arterial and venous patient lines 256, 258 of the blood component set 264 are connected to a patient and blood is circulated through various blood lines and components, including a dialyzer 260, of the blood component set 264. At the same time, dialysate is circulated through a dialysate circuit formed by the dialyzer 260 and various other dialysate components and dialysate lines connected to the HD machine 252. Many of these dialysate components and dialysate lines are located inside the housing 253 of the HD machine 252, and are thus not visible in FIG. 2B. The dialysate passes through the dialyzer 260 along with the blood. The blood and dialysate passing through the dialyzer 260 are separated from one another by a semi-permeable structure (e.g., a semi-permeable membrane and/or semi-permeable microtubes) of the dialyzer 260. As a result of this arrangement, toxins are removed from the patient's blood and collected in the dialysate. The filtered blood exiting the dialyzer 260 is returned to the patient. The dialysate that exits the dialyzer 260 includes toxins removed from the blood and is commonly referred to as "spent dialysate." The spent dialysate is routed from the dialyzer 260 to a drain.

One of the components of the blood component set 264 is an air release device 262. The air release device 262 includes a self-sealing vent assembly that allows air to pass through while inhibiting (e.g., preventing) liquid from passing through. As a result, if blood passing through the blood circuit during treatment contains air, the air will be vented to atmosphere as the blood passes through the air release device 262.

As shown in FIG. 2B, a dialysate container 274 is connected to the HD machine 252 via a dialysate supply line 276. A drain line 278 and an ultrafiltration line 279 also extend from the HD machine 252. The dialysate supply line 276, the drain line 278, and the ultrafiltration line 279 are fluidly connected to the various dialysate components and dialysate lines inside the housing 253 of the HD machine 252 that form part of the dialysate circuit. During hemodialysis, the dialysate supply line 276 carries fresh dialysate from the dialysate container 274 to the portion of the dialysate circuit located inside the HD machine 252. As noted above, the fresh dialysate is circulated through various dialysate lines and dialysate components, including the dialyzer 260, that form the dialysate circuit. As the dialysate passes through the dialyzer 260, it collects toxins from the patient's blood. The resulting spent dialysate is carried from the dialysate circuit to a drain via the drain line 278. When ultrafiltration is performed during treatment, a combination of the spent dialysate and excess fluid drawn from the patient is carried to the drain via the ultrafiltration line 279.

The blood component set 264 is secured to a module 280 attached to the front of the HD machine 252. The module 280 includes a blood pump 282 capable of driving blood through the blood circuit. The module 280 also includes various other instruments capable of monitoring the blood flowing through the blood circuit. The module 280 includes a door that when closed, as shown in FIG. 2B, cooperates with the front face of the module 280 to form a compartment sized and shaped to receive the blood component set 264. In the closed position, the door presses certain blood components of the blood component set 264 against corresponding instruments exposed on the front face of the module 280. Such an arrangement facilitates control of the flow of blood through the blood circuit and monitoring of the blood flowing through the blood circuit.

The blood pump 282 can be controlled by a blood pump module 284. The blood pump module 284 includes a display window, a start/stop key, an up key, a down key, a level adjust key, and an arterial pressure port. The display window displays the blood flow rate setting during blood pump operation. The start/stop key starts and stops the blood pump 282. The up and down keys increase and decrease the speed of the blood pump 282. The level adjust key raises a level of fluid in an arterial drip chamber.

A drug pump 286 also extends from the front of the HD machine 252. The drug pump 286 is a syringe pump that includes a clamping mechanism configured to retain a syringe 288 of the blood component set 264. The drug pump 286 also includes a stepper motor configured to move the plunger of the syringe 288 along the axis of the syringe 288. A shaft of the stepper motor is secured to the plunger in a manner such that when the stepper motor is operated in a first direction, the shaft forces the plunger into the syringe 288, and when operated in a second direction, the shaft pulls the plunger out of the syringe 288. The drug pump 286 can thus be used to inject a liquid drug (e.g., heparin) from the syringe 288 into the blood circuit via a drug delivery line 290 during use, or to draw liquid from the blood circuit into the syringe 288 via the drug delivery line 290 during use.

The HD machine 252 includes a touch screen 268 and a control panel 270. The touch screen 268 and the control panel 270 allow an operator to input various treatment parameters to the HD machine 252 and to otherwise control the HD machine 252. In addition, the touch screen 268 serves as a display. The touch screen 268 functions to provide information to the patient and the operator of the HD system 250. For example, the touch screen 268 may display information related to a dialysis treatment to be applied to the patient, including information related to a prescription.

The HD machine 252 includes a processing module 251 that resides inside the machine and which is configured to communicate with the touch screen 268 and the control panel 270. The processing module 251 is configured to receive data from the touch screen 268 and the control panel 270 and control the HD machine 252 based on the received data. For example, the processing module 251 can adjust the operating parameters of the HD machine 252.

The HD machine 252 is configured to connect to a network 254. The HD machine 252 includes a transceiver 255 that is configured to facilitate the connection to the network 254. Other medical devices (e.g., peripheral devices or monitors, other dialysis machines, etc.) may be configured to connect to the network 254 and communicate with the HD machine 252. Similarly, one or more remote entities, such as issuers of digital prescription files, may be able to connect to the network 254 and communicate with the HD machine 252 in order to provide digital prescriptions for implementing on the HD machine 252.

Figure 4:
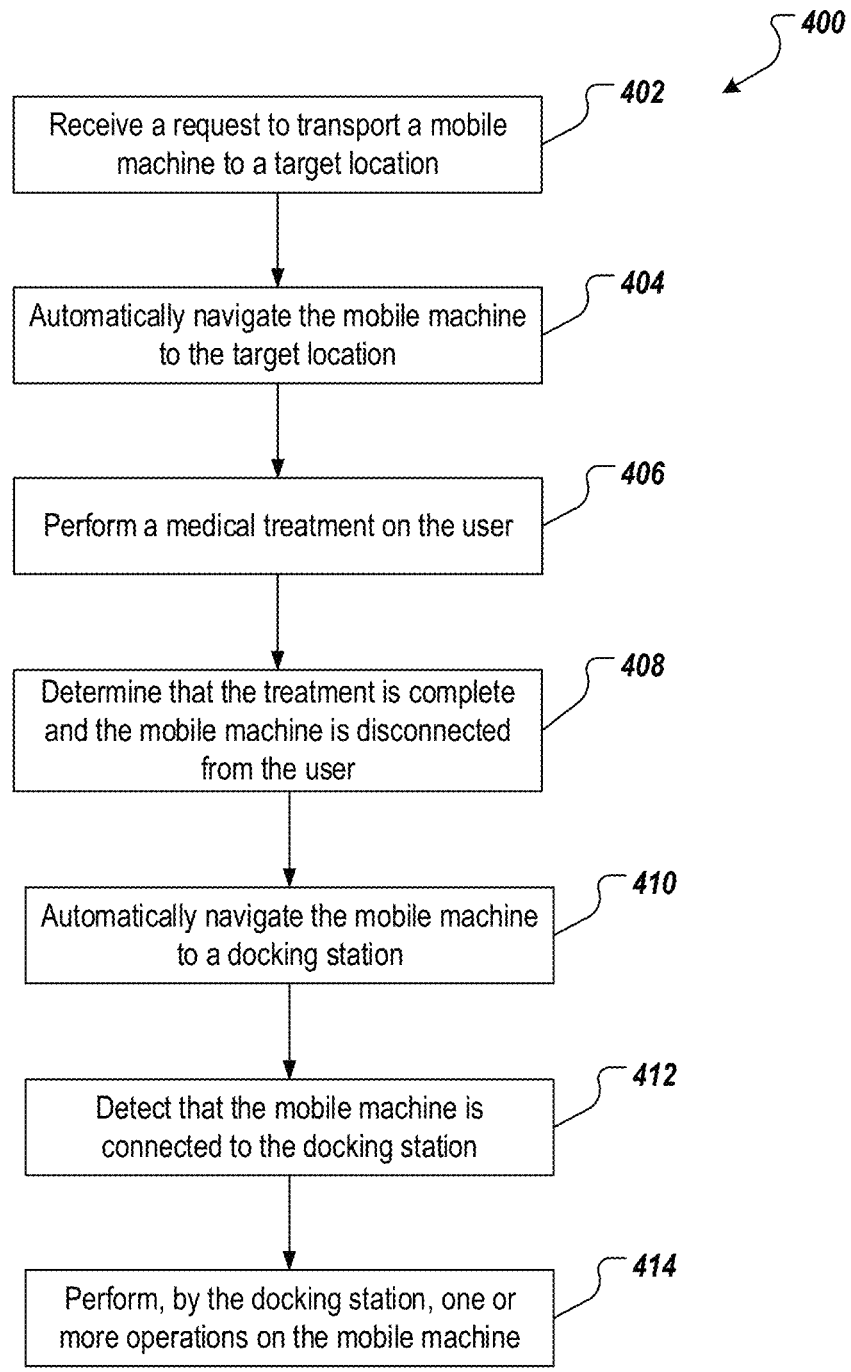
FIG. 4 depicts an example process that can be executed according to implementations of the present disclosure.

FIG. 4 depicts an example process 400 that can be executed according to implementations of the present disclosure. The process 400 can be performed by any of the medical systems described herein.

In the process 400, a request to transport a mobile machine (e.g., the mobile machine 104 of FIG. 1A or the mobile machine 302 of FIG. 3) to a target location is received (402). For example, the request can be received by any part of the medical system, such as the docking station (e.g., the docking station 106 of FIG. 1A) or the mobile machine. The request can be a request to summon received from a user of the medical system, e.g., through voice recognition or an electronic device (e.g. the electronic device 112 of FIG. 1) of the user. The mobile machine includes a medical device that the user can use to perform a medical treatment at the target location.

In response to the request, the mobile machine automatically navigates to the target location (404). The mobile machine can find its path to the target location based on a map input (e.g., downloaded) on the mobile machine. The mobile machine can include one or more sensors to detect barriers and/or a particular signs or colors used by the user to tag or mark the path or an object detectable by the mobile machine as the target location.

The mobile machine performs a medical treatment on the user (406). The medical treatment can include measuring, monitoring, and/or treating the user for a medical issue such as a chronic disease. For example, the mobile machine can include a medical device, such as a HD machine or a PD machine, that the user can use to perform a medical treatment.

The mobile machine can determine that the treatment is completed and the mobile machine is safely disconnected from the user (408). For example, the mobile machine can determine that the medical device was used for more than a predetermined period of time to perform the medical treatment (e.g., more than an hour for a single dialysis operation), and/or detect that tubes, pads, or any other components of the medical device are safely detached from the user's body. Each of such components may have a respective sensor (e.g., temperature sensor, pressure sensor, etc.) configured to detect that the component is detached from the user's body.

The mobile machine can automatically navigate its way to a docking station (410). For example, the mobile machine 104 in FIGS. 1A and 1B can navigate its way to the docking station 106. The mobile machine can navigate its way to the docking station after each medical treatment session, or in response to determining that one or more of the mobile machine's waste containers are filled beyond a predetermined threshold volume and/or one or more of its supply containers are running low (i.e., getting lower than a predetermined threshold volume or amount).

Once the mobile machine is properly connected to the docking station, the docking station performs one or more operations on the mobile machine (412 and 414). For example, the docking station can clean, refill, recharge, and/or drain waste from the mobile machine. Either the docking station or the mobile machine can detect that the mobile machine is properly connected to the docking station (412). For example, prior to performing an operation on the mobile machine, the docking station may determine that the connections required for such operations are properly made between the mobile machine and the docking station. For example, the docking station may check the electrical connections, drain tube connections, and water tubes between the docking station and the mobile machine before respectively performing electrical charging, waste draining, and cleaning (at least part of) the mobile machine.

Figure 5:
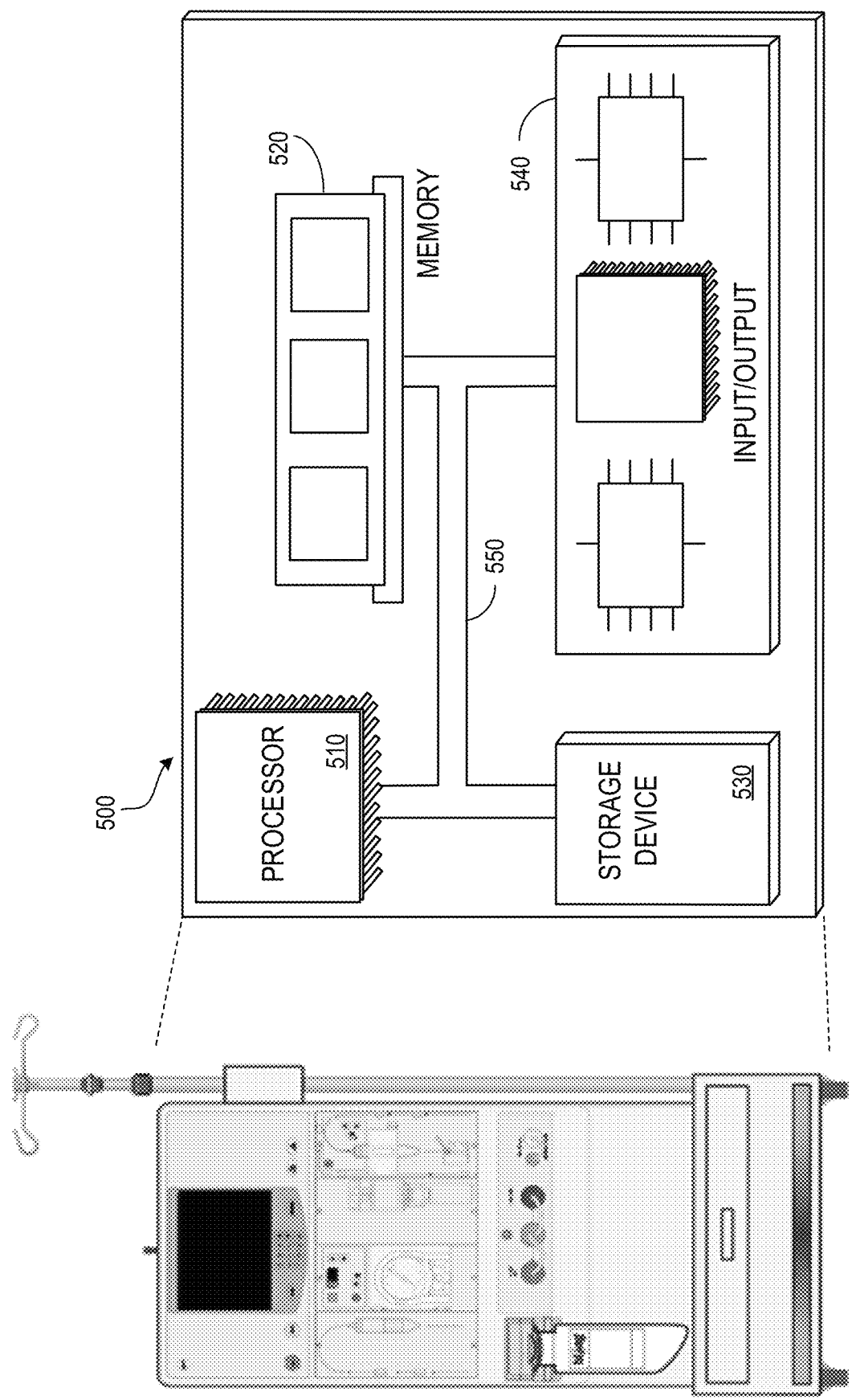
FIG. 5 is a block diagram of an example computing system, according to implementations of the present disclosure.

FIG. 5 is a block diagram of an example computing system 500 that can be used as part of the medical system 102, for example to perform functions of the mobile machine and/or the docking station. The example computing system 500 is illustrated in connection with the mobile machine 302, but the similar components can be used for implementing any part of the medical devices disclosed herein, e.g., the docking station 106 or the mobile machine 104 of FIG. 1A.

A control unit, a computing device, a processor, and/or a microcontroller as described above could be examples of the system 500 described with respect to FIG. 5. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. The processor 510 can be a single-threaded processor, a multi-threaded processor, or a quantum computer. The processor 510 is capable of processing instructions stored in the memory 520 or on the storage device 530. The processor 510 may execute operations such as causing the dialysis system to carry out dialysis functions.

The memory 520 stores information within the system 500. In some implementations, the memory 520 is a computer-readable medium. The memory 520 can, for example, be a volatile memory unit or a non-volatile memory unit. In some implementations, the memory 520 stores information for causing the pumps of the dialysis system to operate as described herein.

The storage device 530 is capable of providing mass storage for the system 500. In some implementations, the storage device 530 is a non-transitory computer-readable medium. The storage device 530 can include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network.

The input/output device 540 provides input/output operations for the system 500. In some implementations, the input/output device 540 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device 540 may include short-range wireless transmission and receiving components, such as Wi-Fi, Bluetooth, and/or near field communication (NFC) components, among others. In some implementations, the input/output device includes driver devices configured to receive input data and send output data to other input/output devices, e.g., keyboard, printer and display devices (such as the touch screen display 268). In some implementations, mobile computing devices, mobile communication devices, and other devices are used.

In some implementations, the system 500 is a microcontroller. A microcontroller is a device that contains multiple elements of a computer system in a single electronics package. For example, the single electronics package could contain the processor 510, the memory 520, the storage device 530, and input/output devices 540.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method executed by one or more processors of a medical system, the method comprising:
   receiving, by a mobile machine of the medical system and from a user, a request to transport the mobile machine to a target location to perform a medical treatment;
   automatically navigating the mobile machine to the target location;
   causing the mobile machine to perform the medical treatment on a patient at the target location;
   determining, by the mobile machine, that the medical treatment is completed and the mobile machine is disconnected from the patient, wherein the determining is at least partly by determining that the mobile machine was used at the target location for more than a predetermined period of time to perform the medical treatment;
   automatically navigating the mobile machine to a stationary docking station of the medical system; and
   determining that the mobile machine is connected to the docking station through one or more connectors, and in response, causing the mobile machine to receive a service comprising at least one of a refill of one or more supplies, a cleaning, or a drain of waste, wherein the one or more connectors include at least one tube for passing liquid during the refill, the cleaning, or the draining.

2. The method of claim 1, wherein the mobile machine comprises a base machine and a medical treatment device, wherein the base machine transports the medical treatment device from the target location to the docking station.

3. The method of claim 1, wherein the mobile machine comprises at least one of a hemodialysis machine or a peritoneal dialysis machine.

4. The method of claim 1, further comprising automatically transporting the mobile machine to a storage area designated for storing the mobile machine, the storage area being different from the target location.

5. The method of claim 1, further comprising:
   determining that the waste does not have any hazardous material from among one or more predetermined materials, and in response, causing the waste to be drained from the mobile machine into a primary reservoir.

6. The method of claim 1, further comprising:
   determining that a supply of medical material in a supply container is below a threshold amount, and in response, providing an alert.

7. The method of claim 1, wherein the mobile machine automatically connects to the docking station through one or more electrical connectors and the at least one tube.

8. The method of claim 1, wherein the mobile machine receives the request from an electronic device though a wireless network.

9. A computer-implemented medical system comprising:
   a stationary docking station; and
   a mobile machine including one or more processors, the mobile machine being connectable to the docking station through one or more connectors, the mobile machine comprising a medical treatment device operable to perform a medical treatment on a patient, wherein the one or more processors are configured to perform operations comprising:
   receiving, from a user, a request to transport the mobile machine to a target location to perform a medical treatment,
   automatically navigating to the target location,
   causing the medical treatment device to perform the medical treatment on the patient at the target location,
   determining that the medical treatment is completed and the mobile machine is disconnected from the patient, wherein the determining is at least partly by determining that the mobile machine was used at the target location for more than a predetermined period of time to perform the medical treatment, and
   automatically navigating to the docking station, and
   wherein the docking station is configured to perform operations comprising:
   determining that the mobile machine is connected to the docking station through the one or more connectors, and in response, causing the mobile machine to receive a service comprising at least one of a refill of one or more supplies, a cleaning, or a draining of waste, wherein the one or more connectors include at least one tube for passing liquid during refilling, cleaning, or draining.

10. The system of claim 9, wherein the mobile machine further comprises a base machine, and wherein the operations cause the base machine to transport the medical treatment device.

11. The system of claim 9, wherein the mobile machine comprises at least one of a hemodialysis machine or a peritoneal dialysis machine.

12. The system of claim 9, wherein the mobile machine is configured to automatically transfer the mobile machine to a storage area designated for storing the mobile machine, the storage area being different from the target location.

13. The system of claim 9, wherein the docking station is configured to perform operations comprising:
   determining that the waste does not have any hazardous material from among one or more predetermined materials, and in response, causing the waste to be drained from the mobile machine into a primary reservoir.

14. The system of claim 9, wherein the mobile machine or the docking station is configured to detect that a supply in a supply container is lower than a threshold volume or amount, and in response, providing an alert.

15. The system of claim 9, wherein the mobile machine automatically connects to the docking station through one or more electrical connectors and the at least one tube.

16. One or more non-transitory computer-readable mediums storing one or more instructions executable by a medical system to perform operations comprising:
   receiving, by a mobile machine of the medical system and from a user, a request to transport the mobile machine to a target location to perform a medical treatment;
   automatically navigating the mobile machine to the target location;
   causing the mobile machine to perform the medical treatment on a patient at the target location;
   determining, by the mobile machine, that the medical treatment is completed and the mobile machine is disconnected from the patient, wherein the determining is at least partly by determining that the mobile machine was used at the target location for more than a predetermined period of time to perform the medical treatment;

automatically navigating the mobile machine to a stationary docking station of the medical system; and determining that the mobile machine is connected to the docking station through one or more connectors, and in response, causing the mobile machine to receive a service comprising at least one of a refill of one or more supplies, a cleaning, or a drain of waste, wherein the one or more connectors include at least one tube for passing liquid during the refill, the cleaning, or the draining.

17. The one or more non-transitory computer-readable mediums of claim 16, wherein the mobile machine comprises a base machine and a medical treatment device, and wherein the operations cause the base machine to transport the medical treatment device.

18. The one or more non-transitory computer-readable mediums of claim 16, wherein the mobile machine comprises at least one of a hemodialysis machine or a peritoneal dialysis machine.

19. The one or more non-transitory computer-readable mediums of claim 16, wherein the operations further comprise:
determining that the waste does not have any hazardous material from among one or more predetermined materials, and in response, draining the waste from the mobile machine into a primary reservoir.

20. The one or more non-transitory computer-readable mediums of claim 16, wherein the operations further comprise:
determining that a supply in a supply container is lower than a threshold volume or amount, and in response, providing an alert.

21. The method of claim 1, further comprising receiving, by the mobile machine, an electric charge in response to determining that the mobile machine is connected to the docking station through the one or more connectors.

22. The method of claim 1, further comprising determining that the waste includes at least one hazardous material from among the one or more predetermined materials, and in response, causing the waste to be drained to a secondary reservoir designated for hazardous material and different from a primary reservoir used for draining non-hazardous wastes.

23. The system of claim 9, wherein the docking station is configured to perform operations comprising determining that the waste includes at least one hazardous material from among the one or more predetermined materials, and in response, causing the waste to be drained to a secondary reservoir designated for hazardous material and a primary reservoir used for draining non-hazardous wastes.

24. The one or more non-transitory computer-readable mediums of claim 16, wherein the operations further comprise determining that the waste includes at least one hazardous material from among the one or more predetermined materials, and in response, causing the waste to be drained to a secondary reservoir designated for hazardous material and a primary reservoir used for draining non-hazardous wastes.

* * * * *